United States Patent [19]

Kakeya et al.

[11] 4,442,090

[45] Apr. 10, 1984

[54] ABSORPTION-PROMOTING COMPOUNDS, COMPOSITIONS THEREOF WITH PHARMACEUTICALS AND/OR BASES FOR RECTAL ADMINISTRATION AND METHOD OF USE

[75] Inventors: Nobuharu Kakeya, Nagaokakyo; Kazuhiko Kitao; Ken-ichi Nishimura, both of Kyoto, all of Japan

[73] Assignee: Kyoto Yakuhin Kogyo Kabushiki Kaisha, Japan

[21] Appl. No.: 246,953

[22] Filed: Mar. 24, 1981

[30] Foreign Application Priority Data

Nov. 14, 1980 [JP] Japan ............................ 55-161121
Nov. 19, 1980 [JP] Japan ............................ 55-157170

[51] Int. Cl.³ .................... A61K 37/26; A61K 37/00; A61K 31/54; A61K 31/425
[52] U.S. Cl. .................................... 424/178; 424/177; 424/180; 424/181; 424/183; 424/203; 424/246; 424/251; 424/274; 424/270; 424/248.5; 424/248.54; 424/248.55; 424/358; 424/DIG. 15

[58] Field of Search ............... 424/178, DIG. 15, 315, 424/319, 246, 270, 248.55, 248.54, 248.5, 180, 177, 183, 181, 274, 203, 251, 358

[56] References Cited

U.S. PATENT DOCUMENTS 4,277,465  7/1981  Kamada ............................ 424/178
4,338,306  7/1982  Kitao et al. ...................... 424/178

*Primary Examiner*—Frederick E. Waddell
*Attorney, Agent, or Firm*—Berman, Aisenberg & Platt

[57] ABSTRACT

Compounds satisfying four specific requirements, namely: (1) a log P value in the range of from 2.5 to 6, (2) a molecular structure with at least one carboxyl group, (3) a pKa value for the carboxyl group of not less than 2.5 and (4) absence of halo substitution, and non-toxic salts thereof promote absorption of pharmacologically-active substance through the rectum into the bloodstream and are effective to raise the concentration of such active substance in the bloodstream even when the active substance is usually unabsorbable or absorbable through the rectum only with considerable difficulty. The compounds are combined with pharmacologically-active ingredients, with pharmaceutical bases suitable for rectal administration of drugs and with appropriate combinations of both.

10 Claims, No Drawings

ABSORPTION-PROMOTING COMPOUNDS, COMPOSITIONS THEREOF WITH PHARMACEUTICALS AND/OR BASES FOR RECTAL ADMINISTRATION AND METHOD OF USE

This invention relates to base compositions for preparations for rectal application, to preparations for rectal application, and to a method of promoting absorption of a pharmacologically-active substance through the rectum into the blood.

For promoting absorption of pharmacologically-active substances through the rectum, it has so far been proposed to add to preparations thereof some compounds capable of promoting absorption of the active substances.

However, such absorption-promoting compounds are not always satisfactory, having several problems. Thus, for example, (1) they are toxic, (2) they are irritating to the rectum, (3) they damage the nucous membrane of the rectum, or (4) they cannot raise the blood level of a pharmacologically-active substance to a level sufficient for the treatment or prophylaxis of a disease.

Under these circumstances, the present inventors have conducted extensive research and have found that, when a pharmacologically-active substance is administered rectally in the presence of a compound satisfying four specific requirements, namely: (1) the log P value is in the range of 2.5 to 6, (2) it contains at least one carboxyl group, (3) the pKa value of the carboxyl group is not less than 2.5 and (4) it does not contain any halogen atoms [such compound hereinafter called Compound (I)], or a nontoxic salt thereof, the pharmacologically-active substance is very easily absorbed through the rectum into the bloodstream, even when the pharmacologically-active substance is one known or supposed to be rectally unabsorbable or to be rectally absorbable only with considerable difficulty or to an inadequate degree. It has also been found that said Compound (I) and nontoxic salts thereof are safely administered rectally to warm-blooded animals, including humans, without much irritation of the rectum or damage to the mucous membrane of the rectum. These findings and further studies have led to the present invention.

Thus, the present invention provides preparations for rectal application which comprise a suitable amount of a pharmacologically-active substance and at least one Compound (I) and/or a nontoxic salt thereof in an amount sufficient to promote absorption of the pharmacologically-active substance, base compositions for preparations for rectal application which comprise a base and at least one Compound (I) and/or nontoxic salt thereof in an amount sufficient to promote absorption and which are capable of promoting absorption of pharmacologically-active substances, and a method of promoting absorption of a phramacologically-active substance through the rectum into the bloodstream which comprises rectally administering the pharmacologically-active substance together with at least one Compound (I) and/or nontoxic salt thereof in an amount sufficient to promote absorption of the pharmacologically-active substance.

Compound (I) and nontoxic salts thereof function as absorption-promoting agents which promote absorption of pharmacologically-active substances through the rectum. Thus, for example, improved base compositions for preparations for rectal application, which are capable of promoting absorption of pharmacologically-active substances, are obtained by incorporating Compound (I) or a nontoxic salt thereof in a base for preparations for rectal application. Furthermore, preparations for rectal application which are excellent in absorbability of pharmacologically-active substances concomitantly present are obtained by manufacturing preparations for rectal application which contain Compound (I) or a nontoxic salt thereof together with the pharmacologically-active substance in the presence or absence of a base.

The log P value for Compound (I), which is the logarithm of the coefficient of distribution of Compound (I) in neutral molecule form between n-octanol and water, is determined, e.g., by the method of Hansch et al. [C. Hansch and T. Fujita, *J. Amer. Chem. Soc.*, 86, 1616 (1964)]. In accordance with the present invention, the log P value should be from 2.5 to 6, preferably from 3 to 6.

Compound (I) contains at least one, generally from 1 to 4, preferably 1 or 2, carboxyl groups.

The pKa value for the carboxyl group or groups should be not less than 2.6, preferably not less than 3.

It is preferable that Compound (I) does not contain any basic group, such as pyridinium or N,N-dimethylaminoethyl, with a pKa of at least 7.

It is also preferable that Compound (I) does not contain any strongly acidic group, e.g. sulfonic acid group or phosphoric acid group, with a pKa of not more than 2, except for carboxyl.

Furthermore, it is essential that Compound (I) does not contain any halogen atom, e.g. chlorine or fluorine.

Generally, Compound (I) has a molecular weight of not more than 1,000, preferably not more than 600.

The nontoxic salts of Compound (I) are, for example, alkali-metal salts (e.g. lithium, sodium or potassium salt), alkaline-earth-metal salts (e.g. magnesium, calcium or barium salt) and salts with organic bases, such as basic amino acids (e.g. lysine or arginine) and organic amines (e.g. dimethylamine or pyridine).

Compound (I) includes, among others, the following groups of compounds:

(1) An N-acylamino acid containing not less than 9 carbon atoms, the acyl moiety being carboxylic acid or carbonic acid acyl and containing from 2 to 18 carbon atoms [hereinafter also called Compound (a)].

The amino acid moiety of Compound (a) must meet only two requirements; it must contain at least one amino group and at least one carboxyl group in its structure. When the amino acid moiety contains two or more carboxyl groups, the carboxyl groups are, optionally, partly amidated or esterified. Examples of the amino acid constituting the amino acid moiety are aliphatic amino acids (e.g. glycine, alanine, valine, leucine or isoleucine), aromatic amino acids (e.g. phenylglycine, phenylanine, tyrosine or tryptophan), hydroxy-amino acids (e.g. serine or threonine), sulfur-containing amino acids (e.g. cysteine, cystine or methionine), acidic amino acids (e.g. aspartic acid or glutamic acid) and amides of acidic amino acids (e.g. asparagine or glutamine).

In Compound (a), the acyl moiety is bonded to the amino group of the previously-mentioned amino acid. In case the amino acid contains two or more amino groups, all or some of the amino groups are optionally acylated. One amino group may be bonded to two acyl groups. The acyl group is, e.g., represented by the formula A—CO—, wherein A is an aliphatic hydrocarbon residue containing from 1 to 17 carbon atoms or an aryl or aralkyl group optionally substituted by at least one substituent selected from the group consisting of hydroxyl, alkyl and alkoxy groups. The aliphatic hydrocarbon residue containing from 1 to 17 carbon atoms is straight-chained or branched and saturated or unsaturated. Preferably, it is a saturated straight-chain group. The aryl or aralkyl group, including any substituent or substituents, contains, e.g., from 6 to 17 carbon atoms. The aryl group is, for example, phenyl, and the aralkyl group is, for example, benzyl or phenethyl. Any substituent alkyl or alkoxy group on the aryl or aralkyl group contains, e.g., from 1 to 8 carbon atoms. The preferred number of carbon atoms contained in said acyl group depends on the kind of amino acid to which it is bonded and is determined by the log P value; Compound (a) has a log P value of from 2.5 to 6, preferably from 3 to 6.

Typical representative of Compound (a) in the practice of the present invention are, for example, compounds of the formula

(a')

wherein $R^a$ is a hydrogen atom or an alkyl, aryl, aralkyl or heterocyclic group, and A—CO— is as defined above. When $R^a$ is an alkyl group, it is optionally bonded to the N atom to form a heterocycle. Said alkyl, aryl, aralkyl or heterocyclic group is, e.g., substituted by a hydroxyl group, a mercapto group optionally substituted by an alkyl group, a —$COR^c$ group (wherein $R^c$ is an amino or hydroxyl group), or an —$NHR^d$ group [wherein $R^d$ is a hydrogen atom, a carbonic acid or carboxylic acid acyl group or —C(—$NH_2$)(=NH)]. When $R^a$ is a group substituted by a mercapto group, Compound (a') is, optionally, in a bis form with said mercapto group serving as the connecting member.

As regards $R^a$, the alkyl group is either straight-chain or branched and is, for example, a lower alkyl containing from 1 to 6 carbon atoms, such as methyl, ethyl, n-propyl, i-propyl, n-butyl, t-butyl or n-pentyl.

As regards $R^a$, the aryl group is, for example, phenyl or naphthyl.

As regards $R^a$, the aryl moiety of the aralkyl group is, for example, phenyl or naphthyl, and the alkylene moiety, such as methylene, ethylene or propylene, contains, for example, from 1 to 4 carbon atoms. Especially preferred examples of the aralkyl group are benzyl and phenethyl.

As regards $R^a$, the heterocyclic group is, e.g., a 5 or 6 membered mono-ring or a condensed ring of side mono-rings and preferably contains 1 or 2 N atoms; it is, for example, indolyl, imidazolyl.

As regards $R^a$, the heterocycle formed by the alkyl group being bonded to the N atom is, for example, a five-membered ring, such as a pyrrole or pyrrolidine ring.

As regards $R^d$, the acyl group is, e.g., one similar to the A—CO— group, and preferably contains from 2 to 10 carbon atoms.

The alkyl group of the "mercapto group optionally substituted by an alkyl group" which is a substituent of $R^d$ is, e.g., one similar to the alkyl group previously mentioned with respect to $R^a$.

Examples of the Compound (a) are N-lauroyl-L-threonine, N-lauroyl-DL-threonine, N-lauroyl-phenylalanine, N-lauroyl-L-valine, N-myristoyl-L-phenylalanine, N-myristoyl-L-valine, N-myristoyl-L-threonine, N-palmitoyl-L-phenylalanine, N-palmitoyl-L-valine, N-palmitoyl-DL-valine, N-palmitoyl-L-threonine, N-palmitoyl-L-aspartic acid, N-palmitoyl-L-leucine, N-palmitoyl-DL-isoleucine, N-palmitoyl-L-tryptophan, N,N'-dipalmitoyl-L-lysine, N-palmitoyl-DL-methionine, N-stearoyl-L-phenylalanine, N-stearoyl-L-valine, N-stearoyl-L-threonine, N-propionoyl-L-phenylalanine, N-butyryl-L-phenylalanine, N-butyryl-L-valine, N-caproyl-L-phenylalanine, N-caproyl-L-valine, N-capropyl-DL-methionine, N-caproyl-L-tryptophan, N-caproyl-L-leucine, N-caproyl-DL-isoleucine, N,N'-dicaproyl-L-lysine, N-caproyl-DL-threonine, N-caproyl-L-phenylalanine, N-capryloyl-L-valine, N-capryloyl-DL-threonine, N-caprinoyl-L-phenylalanine, N-caprinoyl-DL-threonine, N-caprinoyl-L-valine, N-(2-hydroxybenzoyl)phenylalanine and N-(4-butoxybenzoyl)phenylalanine.

Generally, Compound (a), Compound (a') and salts thereof are known substances and are produced by methods known per se [e.g. Seikagaku (Biochemistry), vol. 35, No. 2, p. 67–74 (1963)] or modifications thereof, for instance.

(a) A decalincarboxylic acid represented by the general formula

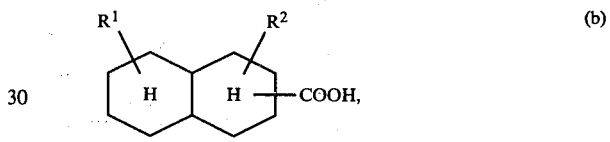

wherein each of $R^1$ and $R^2$ is lower alkyl or a hydrogen atom (—H).

As regards $R^1$ and $R^2$, the lower alkyl contains, e.g., from 1 to 4 carbon atoms and is, for example, methyl, ethyl, n-propyl, i-propyl, n-butyl or t-butyl. Especially preferred is methyl.

Examples of the Decalincarboxylic acid (b) are Decalin-2-carboxylic acid, Decalin-1-carboxylic acid, Decalin-9-carboxylic acid and 4,4-dimethyl-9-carboxyDecalin.

(3) A cyclohexanecarboxylic acid represented by the formula

wherein $R^3$ is a lower alkyl group.

The lower alkyl group, $R^3$, is, e.g., one similar to that represented by $R^1$ or $R^2$.

Examples of the cyclohexanecarboxylic acid (c) are 3-(t-butyl)cyclohexanecarboxylic acid and 4-(t-butyl)-cyclohexanecarboxylic acid.

(4) An aliphatic dicarboxylic acid represented by the formula

wherein $R^4$ is an aliphatic hydrocarbon residue containing from 8 to 14 carbon atoms.

The aliphatic hydrocarbon residue, $R^4$, containing from 8 to 14 carbon atoms, is saturated or unsaturated (double-bonded or triple-bonded) and straight-chain or branched. Preferred are straight-chained and saturated ones containing from 9 to 12 carbon atoms.

Examples of the aliphatic dicarboxylic acid are sebacic acid, 1,9-nonamethylenedicarboxylic acid, 1,10-decamethylenedicarboxylic acid, 1,11-undecamethylenedicarboxylic acid, 1,12-dodecamethylenedicarboxylic acid, 1,13-tridecamethylenedicarboxylic acid, 1,14-tetradecamethylenedicarboxylic acid and $\beta,\beta$-di-(n-propyl)glutaric acid.

(5) A carboxylic acid represented by the formula

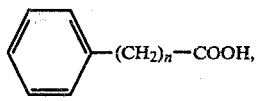  (e)

wherein n is 0 or an integer from 1 to 4, inclusive, the phenyl ring of which is optionally substituted by at least one alkyl or alkoxy group.

The alkyl substituted in Compound (e) is, for example, an alkyl group containing from 1 to 6 carbon atoms, such as methyl, ethyl, n-propyl, i-propyl, n-butyl, i-butyl, n-pentyl or n-hexyl. Especially preferred are alkyl groups containing from 3 to 6 carbon atoms.

The alkoxy substituent in Compound (e) is, for example, an alkoxy group containing from 1 to 6 carbon atoms, such as methoxy, ethoxy, n-propoxy, i-propoxy, n-butoxy, i-butoxy, n-pentyloxy or n-hexyloxy. Especially preferred are alkoxy groups containing from 3 to 6 carbon atoms.

Compound (e) optionally has these substituents in plurality. Thus, for example, it may be disubstituted or trisubstituted. When n is 0, it is preferable that Compound (e) has at least one substituent.

Examples of Compound (e) are 4-butoxybenzoic acid, p-(n-hexyloxy)benzoic acid, 4-butylbenzoic acid, 4-phenyl-n-pentanoic acid and 2,4,6-trimethylbenzoic acid.

(6) A carboxylic acid represented by the formula $$R^5-(OCH_2CH_2)_nO\ CH_2COOH \quad (f),$$

wherein $R^5$ is an alkyl group containing form 8 to 14 carbon atoms and n is an integer from 2 to 6, inclusive.

The alkyl group, $R^5$, containing from 8 to 14 carbon atoms is preferably straight-chained.

An example of Compound (f) is polyoxyethylene stearyl ether carboxylic acid (with 6 moles of ethylene oxide added).

(7) A carboxylic acid represented by the formula

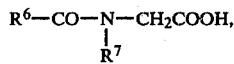  (g)

wherein $R^6$ is an alkyl group containing from 10 to 16 carbon atoms and $R^7$ is a lower alkyl group.

Preferably, the alkyl group, $R^6$, containing from 10 to 16 carbon atoms, is straight-chained.

The lower alkyl group, $R^7$, is, e.g., a lower alkyl group of from 1 to 4 carbon atoms, such as that mentioned with respect to $R^1$ and $R^2$.

An example of the carboxylic acid (g) is N-lauroylsarcosine.

(8) A carboxylic acid represented by the formula $$R^8-OCH_2COOH \quad (h),$$

wherein $R^8$ is an aryl group or an alkyl group containing from 7 to 14 carbon atoms.

The aryl group, $R^8$, includes phenyl, $\alpha$-naphthyl and $\beta$-naphthyl. These are optionally substituted, for example, by an alkyl group of from 1 to 8 carbon atoms, such as methyl, ethyl, n-propyl, i-propyl, n-butyl or octyl. It is preferable that the phenyl group be substituted by an alkyl group of from 3 to 6 carbon atoms, such as a n-propyl, i-propyl, n-butyl or n-hexyl.

The alkyl group, $R^8$, of from 7 to 14 carbon atoms is straight-chained, branched or cyclic and is preferably straight-chained or cyclic, containing from 8 to 12 carbon atoms.

Examples of Compound (h) are $\alpha$-naphthoxyacetic acid and L-menthoxyacetic acid.

(9) A carboxylic acid represented by the formula

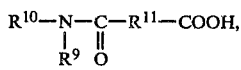  (i)

wherein
$R^9$ is a hydrogen atom (—H) or an alkyl group;
$R^{10}$ is an alkyl group or an aralkyl or aryl group optionally substituted by at least one substituent selected from the group consisting of a hydroxyl group, an alkyl group and an alkoxy group; and
$R^{11}$ is an alkylene or alkenylene group containing 2 or more carbon atoms or a group represented by the formula

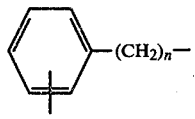

wherein n is an integer of from 0 to 2, inclusive, and optionally substituted by at least one substituent selected from the group consisting of a hydroxyl group, an alkyl group and an alkoxy group.

As regards $R^9$, the alkyl group includes, as preferred embodiments, lower alkyl groups of from 1 to 4 carbon atoms, such as those mentioned with regard to $R^1$ and $R^2$.

As regards $R^{10}$, the alkyl group includes, as preferred embodiments, straight-chain or branched alkyl groups containing from 1 to 10 carbon atoms; the aralkyl group is, for example, benzyl or phenethyl; and the aryl group is, for example, phenyl; the substituent alkyl group on the aralkyl or aryl group includes, as preferred embodiments, straight-chain or branched alkyl groups of from 1 to 8 carbon atoms, and the alkoxy substituents includes, as preferred embodiments, straight-chain or branched alkoxy groups of from 1 to 8 carbon atoms.

As regards $R^{11}$, the alkylene group containing 2 or more carbon atoms includes, as preferred embodiments, straight-chain or branched alkylene groups containing from 2 to 10 carbon atoms, and the alkenylene group containing 2 or more carbon atoms includes, as preferred embodiments, straight-chain or branched alkenylene groups of from 2 to 10 carbon atoms.

The alkyl and alkoxy substituents on the $R^{11}$ group represented by the formula

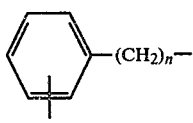

are, e.g., those substituent alkyl and alkoxy groups on the aralkyl or aryl group that are mentioned with respect to $R^{10}$, respectively.

Examples of Compound (i) are N-(n-decyl)succinamic acid, 2-carboxy-N-(n-octyl)benzamide and N,N-di-(n-butyl) succinamic acid.

(10) A carboxylic acid represented by the formula

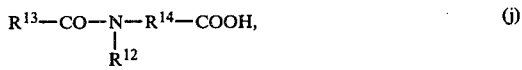

wherein $R^{12}$, $R^{13}$ and $R^{14}$ are defined as $R^9$, $R^{10}$ and $R^{11}$, respectively.

Examples of Compound (j) are N-(n-caprinoyl)-β-alanine, N-(n-caprylyl)-4-aminobenzoic acid and N-(n-caprylyl)-4-methylaminobenzoic acid.

Generally, Compounds (a) to (j) and salts thereof are known compounds, and are prepared by methods known per se or modifications thereof.

Generally, Compound (I) and nontoxic salts thereof in accordance with the present invention, together with a pharmacologically-active substance and other optional substances, are made into preparations for rectal application. They are optionally admixed with conventional bases for rectal administration to prepare improved bases, namely: absorption-promoting base compositions, into which pharmacologically-active substance is subsequently introduced. Compound (I) or a salt thereof alone or in combination with a diluent or vehicle and other optional additives are, alternatively, made into preparations ready for use. What is essential is to apply the pharmacologically-active substance rectally in the presence of Compound (I).

The absorption-promoting base compositions for rectal application in accordance with the present invention include, among others, those compositions comprising bases usable as bases for rectal administration and at least one Compound (I) or nontoxic salt thereof uniformly dispersed therein.

The bases for rectal application include those known per se, such as oleaginous bases and water-soluble bases. The oleaginous bases include vegetable fats and oils, such as cocoa butter, peanut oil, corn oil and fatty acid esters of glycerol [e.g. Witepsol ® (Dynamit-Nobel), SB-Base ® (Kanegafuchi Chemical Industry), O.-D.O ® (Nisshin Seiyu)] and mineral oils, such as vaseline and paraffin. The water-soluble bases are, for example, polyethylene glycol, propylene glycol, glycerin, polyacrylic acid-based hydrous gel and gelatin gel.

The preparations for rectal application in accordance with the present invention are, e.g., in the form of the so-called rectal suppositories or of soft capsules which comprise a suspension of ointment-like dispersion in a liquid oleaginous base, as filled in soft capsules, or other forms.

Such preparations are prepared by combining at least one Compound (I) or nontoxic salt thereof with a pharmacologically-active substance. The preparations optionally contain a base, a surfactant, an antioxidant, a preservative, a diluent or vehicle, etc.

Thus, for example, rectal suppositories are prepared by uniformly dispersing at least one Compound (I) or nontoxic salt thereof in a base, then adding and uniformly dispersing a pharmacologically-active substance and filling suppository containers with the resulting composition to form the desired suppositories. The order of addition is not always or necessarily limited to that mentioned.

In practicing the present invention, any pharmacologically-active substance may be used, so long as it is absorbable into the bloodstream and thus capable of exerting its pharmacological activity. Thus, the pharmacologically-active substances include, e.g., β-lactam antimicrobial agents (e.g. β-lactam antibiotics, such as penicillins and cephalosporins, clavulanic acid and thienamycin, the terms "penicillins" and "cephalosporins" also including within their respective meanings analogs, such as oxa analogs which have an oxygen atom in place of the sulfur atom in the penam and cepham ring structures, respectively), aminoglycoside antibiotics, polysaccharide drugs, peptide drugs, nucleic acid drugs and so forth.

The penicillins include ampicillin, cyclacillin, cloxacillin, benzylpenicillin, carbenicillin, piperacillin, mezlocillin, pirbenicillin, ticarcillin, (2S, 5R, 6R)-6-[(R)-2-(4-hydroxy-1,5-naphthylidine-3-carboxamido)-2-phenylacetamido]-3,3-dimethyl-7-oxo-4-thia-1-azabicyclo[3.2.0]heptane-2-carboxylic acid, and their salts, such as sodium salts, etc.

The cephalosporins include cephalothin, cefoxitin, cefazolin, cephaloridine, cephacetrile, cefotiam, ceforanide, cephanone, cefaclor, cefadroxil, cefatrizine, cefradine, cephaloglycin, 7-[D(−)-α-(4-ethyl-2,3-dioxo-1-piperazinecarboxamido)-α-(4-hydroxyphenyl)acetamido]-3-[(1-methyl-1H-tetrazol-5-yl)thiomethyl]-3-cephem-4-carboxylic acid, (6R, 7R)-[(Z)-2-methoxyimino-2-(2-imino-4-thiazolin-4-yl)acetamido]-8-oxo-5-thia-1-azabicyclo[4.2.0]oct-2-ene-2-carboxylic acid, (6R, 7R)-7-[2-carboxy-2-(4-hydroxyphenyl)acetamido-7-methoxy-3-[(1-methyl-1H-tetrazol-5-yl-thio)methyl]-8-oxo-5-oxa-1-azabicyclo[4.2.0]oct-2-ene-2-carboxylic acid, 7-β-[2-(2-aminothiazol-4-yl)-(Z)-2-methoxyiminoacetamido]-3-[(1-methyl-1H-tetrazol-5-yl)thiomethyl]ceph-3-em-4-carboxylic acid, 7-(2-amino-2-phenylacetamido)-3-methoxy-8-oxo-5-thia-1-azabicyclo[4.2.0]oct-2-ene-2-carboxylic acid, (6R, 7R)-7-[(Z)-2-(2-imino-4-thiazolin-4-yl)-2-methoxyiminoacetamido]-8-oxo-5-thia-1-azabicyclo[4.2.0]oct-2-ene-2-carboxylic acid, 7-β-[2-(2-aminothiazol-4-yl)-(Z)-2-methoxyiminoacetamido]-3-[(1-methyl-1H-tetrazol-5-yl)thiomethyl]ceph-3-em-4-carboxylic acid hemihydrochloride, (6R, 7R)-7-[2-carboxy-2-(4-hydroxyphenyl)acetamido]-7-methoxy-3-[(1-methyl-1H-tetrazol-5-yl-thio)methyl]-8-oxo-5-oxa-1-azabicyclo[4.2.0]oct-2-ene-2-carboxylic acid and their salts, such as sodium salts, etc.

The aminoglycoside antibiotics include, among others, dibekacin, gentamicin, streptomycin, kanamycin, paromomycin, kanendomycin, lividomycin, tobramycin, amikacin, fradiomycin, sisomicin and fortimicin.

The polysaccharide drugs include, among others, heparin and polysaccharide antitumor agents. Examples of the polysaccharide antitumor agents are zymosan, lentinan and PS-K.

The peptide drugs include insulin, angiotensin analogs, ACTH, TRH's [THR, TRH analogs, such as L-N-

(2-oxopiperidine-6-carbonyl)-L-histidyl-L-thiazolidine-4-carboxamide, L-2-oxooxazolidine-4-carbonyl-L-histidyl-L-prolinamide, L-trans-5-methyl-2-oxooxazolidine-4-carbonyl-L-histidyl-L-prolinamide, L-2-oxothiazolidine-4-carbonyl-L-histidyl-L-prolinamide, γ-butyrolactone-γ-carbonyl-L-histidyl-L-prolinamide, 2-ketopiperidine-6-carbonyl-L-histidyl-L-prolinamide and 3-oxoperhydro-1,4-thiazine-5-carbonyl-L-histidyl-L-prolinamide, and derivatives of TRH and TRH analogs in which the hydrogen atom of the amide group thereof is substituted by methyl, ethyl, n-propyl, n-butyl, n-hexyl, n-amyl or β-phenethyl], enkephalin, LH-RH, peptide antibiotics, such as polymyxin B, colistin, gramicidin and bacitracin, peptide antitumor agents, and so forth. Examples of the peptide antitumor agents are bleomycin and neocarzinostatin. The nucleic acid drugs include citicoline, nucleic acid antitumor agents (e.g. 5-FU) and so on.

Other pharmacologically-active substances include mercapto-proline derivatives, such as 3-mercapto-2-methylpropanoyl-proline, fosfomycin, and so on.

It is preferable that the pharmacologically-active substances have an average molecular weight of not more than 12,000, preferably not more than 6,000, more preferably not more than 2,000.

In case the pharmacologically-active substance is a basically-reacting compound, Compound (I) may form a salt with said pharmacologically-active substance. Such a mode of practice is also covered by the present invention.

The percent amount of Compound (I) or a nontoxic salt thereof in a preparation for rectal application in accordance with the present invention depends on the nature of the pharmacologically-active substance and other factors. However, generally, it is from 0.5 to 40% by weight, preferably from 1 to 15% by weight, more preferably from 3 to 10% by weight, based on the weight of the whole preparation.

The amount of Compound (I) or a nontoxic salt thereof in a base composition in accordance with the invention depends on the nature of the base, the nature of the main drug component to be added afterwards and other factors. However, generally, it is from 0.5 to 50% by weight, preferably from 1 to 20% by weight, more preferably from 2 to 13% by weight.

The amount of the pharmacologically-active substance in a preparation for rectal application in accordance with the present invention depends on the nature of the pharmacologically-active substance, the nature of the base, the nature of Compound (I), the subject to which the preparation is to be administered, etc. Generally, however, it is from 20 to 500 mg per gram of the base in the case of a β-lactam antibiotic, from 1 to 80 units per gram of the base in the case of insulin, for instance, from 5 to 100 mg per gram of the base in the case of an aminoglycoside antibiotic, and from 50 to 2,000 thousand units in the case of a peptide antibiotic, such as colistin sodium methanesulfonate. What is essential is that the preparation contain a therapeutically-effective amount of the pharmacologically-active substance.

The examples which follow are presented solely for the purpose of illustration and in no way limit the nature or scope of the invention.

Example 1

7.6 Grams of Witepsol H-15 (a registered mark of Dynamite Nobel) was melted at a temperature not exceeding 40° C. and 1 g of sodium 1,9-nonamethylenedicarboxylate of 100 mesh pass was added and evenly dispersed by stirring to obtain a base containing sodium 1,9-nonamethylenedicarboxylate. Then, 1.4 g of sodium ampicillin (hereinafter referred to briefly as AB-PC) of 100 mesh pass was evenly dispersed. The mixture was molded in suppository containers at the rate of one gram per container to prepare rectal suppositories.

Example 2

Bases and rectal suppositories of the compositions indicated in the Sample Column of Table 1 were prepared in accordance with the procedure of Example 1.

The absorption into the circulation through the rectum of the rectal suppositories thus prepared was determined by measuring urinary excretion of the pharmacologically-active substance.

The results are shown in Table 1.

Method of determination:

Each rectal suppository was administered to a depth of 2 cm from the anus of a rabbit fasted 24 hours.

To measure the urinary excretions, urine samples were collected after administration at timed intervals, diluted and assayed by the biological assay procedure.

Thus, *Sarcina lutea* and *Bacillus subtilis* were used as assay organisms for penicillins and cephalosporins, respectively, and the assays were performed by the paper disk method (cultivation at 37° C. for from 15 to 20 hours).

Example 3

Bases and AB-PC rectal suppositories of the compositions indicated in the Sample column of Table 2 were prepared in accordance with the procedure of Example 1.

The thus-obtained suppositories were administered to healthy adult male humans from the anus, and the urinary excretions of AB-PC were determined.

The results are shown in Table 2.

To measure the urinary excretions, urine sample were collected after administration at timed intervals, diluted and assayed by the procedure described in Example 2.

Comparative Examples 1 to 7 in Table 2 are for the cases where the log P values are out of the range specified in accordance with the present invention, whereas Comparative Examples 8 to 11 are for the cases where the compounds used had no free carboxyl groups or non-toxic salt thereof.

As is evident from Table 2, the preparations of the present invention exhibit very excellent rectal absorbability.

Example 4

Bases and rectal suppositories of the compositions indicated in the Sample column of Table 3 were prepared in accordance with the procedure of Example 1.

The thus-obtained suppositories were administered to healthy adult male humans from the anus, and the urinary excretions of AB-PC were determined.

The results are shown in Table 3.

The test was conducted in the same manner as in Example 2.

Example 5

Bases and rectal suppositories of the compositions indicated in the Sample column of Table 4 were prepared in accordance with the procedure of Example 1.

The thus-obtained suppositories were administered to rabbits from the anus, and the urinary excretions of the pharmacologically-active substance were determined.

The results are shown in Table 4.

Method of determination:

Each rectal suppository was administered to a depth of 2 cm from the anus of a rabbit fasted 24 hours.

To measure the urinary excretions, urine samples were collected after administration at timed intervals, diluted and assayed by the biological assay procedure.

Thus, *Escherichia coli* was used as assay organism and the assays were performed by the cylinder plate method (cultivation at 37° C. for 15 to 20 hours).

Example 6

Bases and rectal suppositories of the compositions indicated in the Sample column of Table 5 were prepared in accordance with the procedure of Example 1.

The thus-obtained suppositories were administered to rabbits and the urinary excretions of the pharmacologically-active substance were determined.

The results are shown in Table 5.

Method of determination:

Each rectal suppository was administered to a depth of 2 cm from the anus of a rabbit fasted 24 hours.

To measure the urinary excretions, urine samples were collected after administration at timed intervals, diluted and assayed by the biological assay procedure.

Thus, *Bacillus subtilis* was used as assay organism and the assays were performed by the cylinder plate method (cultivation at 37° C. for 15 to 20 hours).

Example 7

Bases and rectal suppositories of the compositions indicated in the Sample column of Table 6 were prepared in accordance with the procedure of Example 1.

The thus-obtained suppositories were administered to rabbits, and the blood glucose levels were observed at intervals.

The results are shown in Table 6.

Method of determination:

Each rectal suppository was administered to a depth of 2 cm from the anus of a rabbit fasted 24 hours. To measure glucose levels, blood samples were taken from the auricular vein at timed intervals and assayed by the glucose oxidase method.

In Tables 1 to 6, Compounds 1 to 30 each represent the following compounds:

| Compound No. | Compound | log P-value |
|---|---|---|
| 1 | 1,9-Nonamethylendicarboxylic acid | 3.08 |
| 2 | 1,10-Decamethylenedicarboxylic acid | 3.58 |
| 3 | p-Butoxybenzoic acid | 3.48 |
| 4 | p-Butylbenzoic acid | 3.88 |
| 5 | 1,11-Undecamethylene dicarboxylic acid | 4.08 |
| 6 | p-Hexyloxybenzoic acid | 4.46 |
| 7 | 1,12-Dodecamethylene dicarboxylic acid | 4.58 |
| 8 | α-Napthoxacetic acid | 2.54 |
| 9 | Polyoxyethylene stearyl ether carboxylic acid (with 6 moles of ethylene oxide) | — |
| 10 | N—Lauroylsarcosine | 3.70 |
| 11 | L-Menthoxyacetic acid | 3.40 |
| 12 | N—(n-Decyl)succinamic acid | 3.62 |
| 13 | N—(n-Decyl)maleamic acid | 3.32 |
| 14 | 2-Carboxy-N—(n-octyl)benzamide | 4.36 |
| 15 | N,N—Di-(n-butyl)succinamic acid | 3.96 |
| 16 | N—(n-Caprinoyl)-β-alanine | 4.12 |
| 17 | N—(n-Caprylyl)-4-aminobenzoic acid | 4.23 |
| 18 | N—(n-Caprylyl)-4-methylaminobenzoic acid | 4.73 |
| 19 | N—(2-Hydroxybenzoyl)phenylalanine | 3.82 |
| 20 | N—(4-Butoxybenzoyl)phenylalanine | 4.58 |
| 21 | N—Caproyl-L-phenylalanine | 2.83 |
| 22 | N—Caproyl-L-tryptophan | 2.83 |
| 23 | N—Capryloyl-L-phenylalanine | 3.88 |
| 24 | N—Caprinoyl-L-valine | 3.50 |
| 25 | N—Lauroyl-L-valine | 4.50 |
| 26 | N—Myristoyl-L-threonine | 4.04 |
| 27 | N—Palmitoyl-L-aspartic acid | 4.49 |
| 28 | N—Myristoyl-L-glutamic acid | 3.99 |
| 29 | N—Butyryl-DL-phenylglycine | 2.33 |
| 30 | N—Caprinoyl-L-methionine | 3.65 |

The urinary excretion values in Tables 1 to 5 are percentages based on the dose administered. The blood glucose levels in Table 6 are relative blood glucose levels when the blood glucose level at hour 0 is considered to be 100%.

In the following Tables "Na" indicates sodium salt.

TABLE 1

Urinary Excretions of β-Lactam Antibiotics

| Base | Pharmacologically-active Substance 125 mg (potency) | Compound (I) 5% | 0–2 hr. | 2–4 hr. | 4–6 hr. | Total (0–6 hr.) |
|---|---|---|---|---|---|---|
| Witepsol H-15 | Cephalothin | Compound 1-Na | 20.5 | 3.0 | 0.2 | 23.7 |
| | | Compound 22-Na | 19.5 | 2.5 | 0.2 | 22.2 |
| | Cefazolin | Compound 2-Na | 41.5 | 16.9 | 3.5 | 61.9 |
| | | Compound 22-Na | 40.5 | 16.0 | 2.0 | 58.5 |
| To make a total of 1g | Cefotaxime | Compound 9-Na | 30.9 | 12.2 | 1.5 | 44.6 |
| | | Compound 24-Na | 31.5 | 10.0 | 0.8 | 42.3 |
| | FK-749* | Compound 3-Na | 41.6 | 19.2 | 3.0 | 63.8 |
| | | Compound 12-Na | 40.1 | 18.0 | 2.0 | 60.1 |
| | | Compound 13-Na | 39.1 | 18.0 | 2.1 | 59.2 |
| | | Compound 14-Na | 41.2 | 19.0 | 1.8 | 62.0 |
| | | Compound 24-Na | 45.0 | 5.6 | 2.5 | 53.1 |
| Witepsol H-15 | Cefmetazole | Compound 3-Na | 45.0 | 20.0 | 1.5 | 66.5 |
| | | Compound 15-Na | 44.0 | 20.0 | 1.0 | 65.9 |
| To make a total of 1g | | Compound 16-Na | 43.1 | 19.9 | 2.9 | 69.1 |
| | | Compound 17-Na | 45.0 | 21.1 | 3.0 | 64.6 |
| | | Compound 25-Na | 45.0 | 10.0 | 2.0 | 57.0 |
| | Sulbenicillin | Compound 10-Na | 33.5 | 10.0 | 1.0 | 43.5 |
| | | Compound 26-Na | 40.0 | 5.1 | 1.0 | 46.2 |
| | Cefsulodin | Compound 4-Na | 30.5 | 15.0 | 1.1 | 45.6 |
| | | Compound 26-Na | 41.1 | 8.2 | 0.5 | 49.8 |
| | Cefotiam | Compound 5-Na | 40.0 | 8.0 | 2.1 | 60.1 |
| | | Compound 27-Na | 35.2 | 6.2 | 0.5 | 41.9 |
| | SCE-1365** | Compound 6-Na | 45.0 | 18.2 | 1.8 | 65.0 |
| | | Compound 28-Na | 46.5 | 10.1 | 0.8 | 57.4 |

TABLE 1-continued

Urinary Excretions of β-Lactam Antibiotics

| Sample Pharmacologically-active | | Urinary excretions (%) | | | |
|---|---|---|---|---|---|
| Base | Substance 125 mg (potency) | Compound (I) 5% | 0–2 hr. | 2–4 hr. | 4–6 hr. | Total (0–6 hr.) |
| Witepsol H-15 To make a total of 1g | 6059-S*** | Compound 7-Na | 42.2 | 8.8 | 1.0 | 52.0 |
| | | Compound 29-Na | 47.2 | 8.6 | 2.0 | 57.8 |
| | | Compound 18-Na | 42.2 | 18.8 | 3.6 | 64.6 |
| | | Compound 19-Na | 38.0 | 20.0 | 3.1 | 61.1 |
| | | Compound 20-Na | 46.0 | 15.2 | 4.1 | 65.3 |

*Sodium (6R, 7R)-7-[(Z)-2-(2-imino-4-thiazolin-4-yl)-2-methoxyiminoacetamido]-8-oxo-5-thia-1-azabicyclo[4,2,0]oct-2-ene-2-carboxylate
**7-β-[2-(2-Aminothiazol-4-yl)-(Z)-2-methoxyiminoacetamido]-3-[(1-methyl-1H-tetrazol-5-yl)-thiomethyl]ceph-3-em-4-carboxylic acid hemihydrochloride
***(6R, 7R)-7-[2-Carboxy-2-(4-hydroxyphenyl)acetamido]-7-methoxy-3-[(1-methyl-1H-tetrazol-5-yl-thio)-methyl]-8-oxo-5-oxa-1-azabicyclo[4,2,0]oct-2-ene-2-carboxylic acid disodium salt

TABLE 2

Urinary Excretions of AB-PC after Administration of AB-PC Rectal Suppository (Human)

| | Sample | | | Urinary excretions of |
|---|---|---|---|---|
| | AB-PC · Base | Compound (I) | log P value | AB-PC (%) (0–6 hr.) |
| Present Invention | AB-PC 125 mg (potency) Witepsol H-15 To make a total of 1 g | Compound 8-Na 10% | 2.54 | 15.1 |
| | | Compound 1-Na 10% | 3.08 | 15.2 |
| | | Compound 11-Na 10% | 3.40 | 20.0 |
| | | Compound 2-Na 10% | 3.58 | 25.6 |
| | | Compound 3-Na 10% | 3.48 | 20.9 |
| | | Compound 4-Na 10% | 3.88 | 28.6 |
| | | Compound 5-Na 1% | 4.08 | 30.8 |
| | | Compound 6-Na 10% | 4.46 | 21.2 |
| | | Compound 7-Na 10% | 4.58 | 22.6 |
| Comparative Examples 1-7 | AB-PC 125 mg (potency) Witepsol H-15 To make a total of 1 g | N—Acetylglycine Na 10% | −1.80 | 2.5 |
| | | Acetic acid Na 10% | −0.17 | 3.6 |
| | | P—Aminobenzoic acid Na 10% | 0.97 | 4.9 |
| | | Pimelic acid Na 10% | 1.08 | 6.0 |
| | | Phenylacetic acid Na 10% | 1.41 | 5.8 |
| | | Benzoic acid Na 10% | 1.88 | 5.6 |
| | | Salicylic acid Na 10% | 2.26 | 9.6 |
| Comparative Examples 8-11 | | Acridine 10% | 3.40 | 2.1 |
| | | Benzofurane 10% | 4.15 | 1.9 |
| | | Ethyl caprate 10% | 4.73 | 3.0 |
| | | Ethyl caprylate 10% | 3.73 | 2.9 |

TABLE 3

Urinary Excretions of AB-PC (Human)

| Sample | | Urinary excretions (%) | | | |
|---|---|---|---|---|---|
| Pharmacologically-active substance · Base | Compound (I) | 0–2 (hr.) | 2–4 (hr.) | 4–6 (hr.) | Total (0–6 hr.) |
| AB-PC 125 mg (potency) Witepsol H-15 To make a total of 1 g | Compound 21-Na 10% | 16.8 | 2.0 | 1.1 | 19.9 |
| | Compound 23-Na 10% | 24.0 | 3.0 | 1.2 | 28.2 |
| | Compound 24-Na 10% | 18.0 | 5.1 | 1.0 | 23.1 |
| | Compound 26-Na 10% | 26.1 | 3.0 | 0.9 | 30.0 |
| | Compound 27-Na 10% | 22.0 | 4.1 | 0.7 | 26.8 |
| | Compound 28-Na 10% | 20.0 | 5.0 | 0.8 | 25.8 |

TABLE 4

Urinary Excretions of Peptide Drugs (Rabbit)

| Sample | | Urinary Excretions (%) | | | |
|---|---|---|---|---|---|
| Pharmacologically-active Substance · Base | Compound (I) | 0–2 hr. | 2–4 hr. | 4–6 hr. | Total (0–6 hr.) |
| Colistin Sodium Methanesulfonate 150,000 IU Witepsol H-15 To make a total of 1 g | Compound 2-Na 5% | 20.5 | 9.2 | 1.8 | 31.5 |
| | Compound 23-Na 5% | 21.2 | 10.0 | 1.2 | 32.4 |
| | Compound 23-Na 5% | 18.5 | 8.0 | 0.8 | 27.3 |
| | Compound 30-Na 5% | 19.5 | 11.0 | 0.5 | 31.0 |

TABLE 5

Urinary Excretions of Aminoglycoside Antibiotics

| Sample | | | Urinary excretions (%) | | | |
|---|---|---|---|---|---|---|
| Base | Pharmacologically-active substance | Compound (I) | 0-2 hr. | 2-4 hr. | 4-6 hr. | Total (0-6 hr.) |
| Witepsol H-15 To make a total 1 g | Gentamicin sulfate 125 mg (potency) | Compound 2-Na 5% | 41.2 | 9.9 | 3.1 | 53.2 |
| | | Compound 23-Na 5% | 45.0 | 6.0 | 1.5 | 52.5 |
| | Kanamycin sulfate 125 mg (potency) | Compound 3-Na 5% | 45.1 | 12.2 | 2.6 | 59.8 |
| | | Compound 28-Na 5% | 40.0 | 2.5 | 0.8 | 43.3 |
| | Dibekacin sulfate 125 mg (potency) | Compound 5-Na 5% | 41.1 | 8.8 | 1.1 | 51.0 |
| | | Compound 30-Na 5% | 41.9 | 8.8 | 0.8 | 51.5 |
| | Fortimicin sulfate 125 mg (potency) | Compound 23-Na 5% | 46.0 | 8.0 | 2.0 | 56.0 |

TABLE 6

Blood glucose level after Insulin Administration

| Sample | | Blood glucose level | | | | | |
|---|---|---|---|---|---|---|---|
| Insulin · Base | Compound (I) | 0 hr. | 0.5 hr. | 0.75 hr. | 1.0 hr. | 1.5 hr. | 2.0 hr. |
| Insulin 6 I. U. Witepsol H-15 569.5 mg | Compound 2-Na 5% | 100 | 57.0 | 50.5 | 51.5 | 68.5 | 98.5 |
| | Compound 3-Na 5% | 100 | 60.0 | 51.5 | 50.5 | 79.5 | 103.3 |
| | Compound 5-Na 5% | 100 | 60.0 | 51.7 | 55.2 | 80.5 | 110.3 |
| | Compound 23-Na 5% | 100 | 59.0 | 51.5 | 51.5 | 69.5 | 103.0 |
| | Compound 28-Na 5% | 100 | 57.0 | 51.5 | 52.5 | 80.0 | 99.5 |
| | Compound 29-Na 5% | 100 | 60.0 | 50.6 | 55.0 | 81.2 | 111.3 |

The invention and its advantages are readily understood from the preceding description. Various changes may be made in the absorption-promoting compound (as long as it satisfies the four specified requirements), the pharmacologically-active substance with which it is combined, the base suitable for rectal administration and other administration details without departing from the spirit or scope of the invention or sacrificing its material advantages. The previously-described compounds, bases and compositions are merely illustrative of preferred embodiments of the invention.

What is claimed is:

1. A combination of (I) a physiologically-acceptable pharmacologically-active substance, which is rectally unabsorbable into the bloodstream or rectally absorbable into the bloodstream to an inadequate degree or only with difficulty, with (II) at least one physiologically-acceptable compound which is an N-acylamino acid having at least 9 carbon atoms, the acyl moiety having from 2 to 18 carbon atoms, and which:

(A) has a log P value in the range of from 2.5 to 6,
(B) has at least one carboxyl group in its molecular structure,
(C) has a carboxyl-group pKa value of at least 2.5, and
(D) is free from halogen atoms, or a nontoxic salt thereof;
the amount of (II) being sufficient to promote absorption of (I) from the rectum into the bloodstream.

2. A combination according to claim 1 wherein the compound is one of the formula

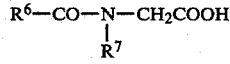

wherein $R^6$ is alkyl with from 10 to 16 carbon atoms, and
$R^7$ is lower alkyl.

3. A combination of (I) a physiologically-acceptable pharmacologically-active substance, which is rectally unabsorbable into the bloodstream or rectally absorbable into the bloodstream to an inadequate degree or only with difficulty, with (II) at least one physiologically-acceptable compound which is one of the formula

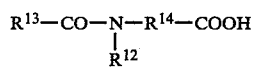

wherein $R^{12}$ is a hydrogen atom (—H) or alkyl;
$R^{13}$ is alkyl, optionally-substituted aralkyl or optionally-substituted aryl, any optional substituent being hydroxyl, alkyl or alkoxy; and
$R^{14}$ is alkylene or alkenylene having at least 2 carbon atoms or a group of the formula

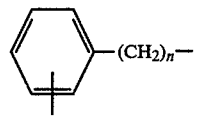

wherein n is 0, 1 or 2, and the phenylene ring is optionally substituted by at least one substituent selected from the group consisting of hydroxyl, alkyl and alkoxy, and which:

(A) has a log P value in the range of from 2.5 to 6,
(B) has at least one carboxyl group in its molecular structure
(C) has a carboxyl-group pKa value of at least 2.5, and
(D) is free from halogen atoms, or a nontoxic salt thereof;
 the amount of (II) being sufficient to promote absorption of (I) from the rectum into the bloodstream.

4. A base suitable for rectal administration of a pharmacologically-active substance and having therein a combination according to one of claims 2 and 3.

5. A base suitable for rectal administration of a pharmacologically-active substance and having incorporated therein at least one physiologically-acceptable compound which is an N-acylamino acid having at least 9 carbon atoms, the acyl moiety having from 2 to 18 carbon atoms, and which:
 (A) has a log P value in the range of from 2.5 to 6,
 (B) has at least one carboxyl group in its molecular structure,
 (C) has a carboxyl-group pKa value of at least 2.5, and
 (D) is free from halogen atoms,
or a nontoxic salt thereof;
 the amount of the compound being sufficient to promote absorption of the pharmacologically-active substance from the rectum into the bloodstream.

6. A base according to claim 5 wherein the compound is one of the formula

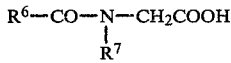

wherein
$R^6$ is alkyl with from 10 to 16 carbon atoms, and
$R^7$ is lower alkyl.

7. A base suitable for rectal administration of a pharmacologically-active substance and having incorporated therein at least one physiologically-acceptable compound which is one of the formula

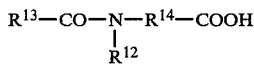

wherein
$R^{12}$ is a hydrogen atom (—H) or alkyl;
$R^{13}$ is alkyl, optionally-substituted aralkyl or optionally-substituted aryl, any optional substituent being hydroxyl, alkyl or alkoxy; and
$R^{14}$ is alkylene or alkenylene having at least 2 carbon atoms or a group of the formula

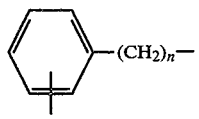

wherein n is 0, 1 or 2, and the phenylene ring is optionally substituted by at least one substituent selected from the group consisting of hydroxyl, alkyl and alkoxy, and which:
 (A) has a log P value in the range of from 2.5 to 6,
 (B) has at least one carboxyl group in its molecular structure,
 (C) has a carboxyl-group pKa value of at least 2.5, and
 (D) is free from halogen atoms,
or a nontoxic salt thereof;
 the amount of the compound being sufficient to promote absorption of the pharmacologically-active substance from the rectum into the bloodstream.

8. A method of promoting absorption of a pharmacologically-active substance through the rectum into the bloodstream of a mammal which comprises rectally administering the pharmacologically-active substance to the mammal together with at least one physiologically-acceptable compound which is an N-acylamino acid having at least 9 carbon atoms, the acyl moiety having from 2 to 18 carbon atoms, and which:
 (A) has a log P value in the range of from 2.5 to 6,
 (B) has at least one carboxyl group in its molecular structure,
 (C) has a carboxyl-group pKa value of at least 2.5, and
 (D) is free from halogen atoms,
or a nontoxic salt thereof;
 the amount of the compound being sufficient to promote absorption of the pharmacologically-active substance from the rectum into the bloodstream.

9. A method according to claim 8 wherein the compound is one of the formula

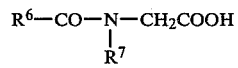

wherein
$R^6$ is alkyl with from 10 to 16 carbon atoms, and
$R^7$ is lower alkyl.

10. A method of promoting absorption of a pharmacologically-active substance through the rectum into the bloodstream of a mammal which comprises rectally administering the pharmacologically-active substance to the mammal together with at least one physiologically-acceptable compound which is one of the formula

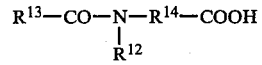

wherein
$R^{12}$ is a hydrogen atom (—H) or alkyl;
$R^{13}$ is alkyl, optionally-substituted aralkyl or optionally-substituted aryl, any optional substituent being hydroxyl, alkyl or alkoxy; and
$R^{14}$ is alkylene or alkenylene having at least 2 carbon atoms or a group of the formula

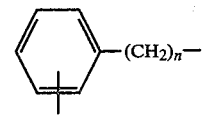

wherein n is 0, 1 or 2, and the phenylene ring is optionally substituted by at least one substituent selected from the group consisting of hydroxyl, alkyl and alkoxy, and which:
 (A) has a log P value in the range of from 2.5 to 6,
 (B) has at least one carboxyl group in its molecular structure,
 (C) has a carboxyl-group pKa value of at least 2.5, and
 (D) is free from halogen atoms,
or a nontoxic salt thereof;
 the amount of the compound being sufficient to promote absorption of the pharmacologically-active substance from the rectum into the bloodstream.

* * * * *

UNITED STATES PATENT AND TRADEMARK OFFICE
CERTIFICATE OF CORRECTION

PATENT NO. : 4,442,090
DATED : April 10, 1984
INVENTOR(S) : NOBUHARU KAKEYA, et al.

It is certified that error appears in the above-identified patent and that said Letters Patent are hereby corrected as shown below:

On the title page;
Item [30], Foreign Application Priority Data, second date, "Nov. 19, 1980" should read --Nov. 9, 1980--

Signed and Sealed this

Eighth Day of October 1985

[SEAL]

Attest:

DONALD J. QUIGG

Attesting Officer

Commissioner of Patents and Trademarks—Designate